United States Patent [19]

Berger et al.

[11] 4,172,136
[45] Oct. 23, 1979

[54] 3-NITROPYRAZOLE COMPOUNDS AND ANTI-MICROBIAL COMPOSITIONS

[75] Inventors: Herbert Berger, Mannheim-Käfertal; Rudi Gall, Hirschberg-Grossachsen; Kurt Stach, deceased, late of Mannheim-Waldhof, Fed. Rep. of Germany, by Werner Plattner, administrator; Max Thiel; Wolfgang Vomel, both of Mannheim, all of Fed. Rep. of Germany

[73] Assignee: Boehringer Mannheim GmbH, Mannheim, Fed. Rep. of Germany

[21] Appl. No.: 889,594

[22] Filed: Mar. 23, 1978

Related U.S. Application Data

[62] Division of Ser. No. 744,215, Nov. 22, 1976, Pat. No. 4,105,772.

[30] Foreign Application Priority Data

Dec. 23, 1975 [DE] Fed. Rep. of Germany ....... 2558117

[51] Int. Cl.$^2$ ................... C07D 401/02; C07D 403/02
[52] U.S. Cl. ..................................... 424/267; 548/377; 424/269; 424/273 P; 542/406; 542/409; 542/410; 542/405
[58] Field of Search .......... 542/405, 406, 409, 410, 411; 548/377; 424/269, 273 P, 267

[56] References Cited

U.S. PATENT DOCUMENTS 3,702,330 11/1972 Hoff et al. .................... 542/406 X
4,066,776 1/1978 Jones et al. .................... 548/377 X

FOREIGN PATENT DOCUMENTS 37-18145 9/1962 Japan ..................... 542/406 X

*Primary Examiner*—Arthur P. Demers
*Attorney, Agent, or Firm*—Sprung, Felfe, Horn, Lynch & Kramer

[57] ABSTRACT

New 3-nitropyrazole compounds of the formula:

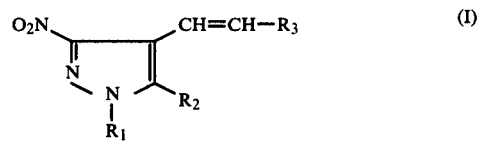

wherein
  $R_1$ is lower alkyl;
  $R_2$ is hydrogen or lower alkyl;
  $R_3$ is cyano, carboxyl or lower alkoxycarbonyl or the radical —CO—NR$_4$R$_5$, in which
  $R_4$ is hydrogen or hydroxyl, carbamoyl, alkylcarbamoyl, dialkylcarbamoyl, thiocarbamoyl, ureido, thioureido, hydroxyphenyl, picolyl or is a lower alkyl, alkenyl or cycloalkyl radical substituted, if desired, by a cyano, hydroxyl, pyrrolidino, piperidino, amino, lower alkylamino, lower dialkylamino or lower acylamino substituent and
  $R_5$ is a hydrogen atom or a lower alkyl radical or
  $R_4$ and $R_5$ together represent a lower alkylene bridge;

and the pharmacologically compatible salts thereof are outstandingly effective as anti-microbial agents, particularly systemically and in the urinary tract.

24 Claims, No Drawings

3-NITROPYRAZOLE COMPOUNDS AND ANTI-MICROBIAL COMPOSITIONS

This is a division, of application Ser. No. 744,215 filed Nov. 22, 1976 now U.S. Pat. No. 4,105,772

The present invention relates to novel 3-nitropyrazole compounds, to anti-microbial compositions containing them and to methods of combatting microbial infections utilizing such compounds.

The 3-nitropyrazole derivatives according to the present invention are compounds of the general formula:

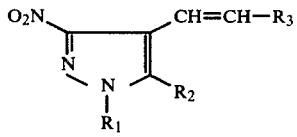

wherein
$R_1$ is lower alkyl;
$R_2$ is hydrogen or lower alkyl;
$R_3$ is cyano, carboxyl or lower alkoxycarbonyl or the radical $-CO-NR_4R_5$, in which
$R_4$ is hydrogen or hydroxyl, carbamoyl, alkylcarbamoyl, dialkylcarbamoyl, thiocarbamoyl, ureido, thioureido, hydroxyphenyl, picolyl or is a lower alkyl, alkenyl or cycloalkyl radical substituted, if desired, by a cyano, hydroxyl, pyrrolidino, piperidino, amino, lower alkylamino, lower dialkylamino or lower acylamino substituent and
$R_5$ is a hydrogen atom or a lower alkyl radical or
$R_4$ and $R_5$ together represent a lower alkylene bridge; and the pharmacologically compatible salts thereof.

We have found that the new compounds according to the present invention have an outstanding anti-microbial action not only in vitro but also in vivo and especially systemically and in the urinary tract.

The alkyl radicals in the definitions of the substituents $R_1$, $R_2$, $R_4$ and $R_5$, as well as the alkoxy radicals in the definition of the substituent $R_3$, can be straight-chained or branched and contain 1 to 5 and preferably 1 to 3 carbon atoms. The methyl, ethyl and isopropyl radicals are especially preferred as alkyl radicals and the methoxy radical is especially preferred as the alkoxy radical.

When $R_4$ is an alkenyl radical, it can contain 2 to 5 and preferably 2 to 3 carbon atoms, when $R_4$ is a cycloalkyl radical, it can contain 3 to 6 carbon atoms and is preferably a cyclopropyl radical, when $R_4$ is an acylamino radical, it can contain 2 to 6 and preferably 2 to 4 carbon atoms, the acetylamino radical being especially preferred, and when $R_4$ and $R_5$ together form an alkylene bridge, it can contain 4 or 5 but preferably 5 carbon atoms.

The new compounds of general formula (I) according to the present invention can be prepared, for example, by one of the following methods:

(a) reaction of a 3-nitro-4-formyl-pyrazole of the general formula:

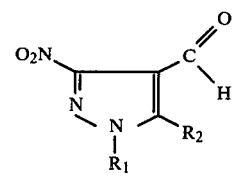

wherein $R_1$ and $R_2$ have the same meanings as above, with a compound of the general formula:

in which X is a hydrogen atom or $R_3$ and $R_3$ has the same meaning as above, and, if X is $R_3$, the product is subsequently decarboxylated, possibly after previous saponification; or (b) reaction of a 3-aminopyrazole derivative of the general formula:

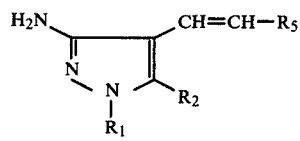

wherein $R_1$, $R_2$ and $R_3$ have the same meanings as above, under the conditions of a nitro Sandmeyer reaction, to give the corresponding nitro compound, whereafter, if desired, in the compound thus obtained of general formula (I), a particular substituent $R_3$ is converted into another substituent $R_3$ by saponification, esterification, transesterification, amidation, transamidation, dehydration, alkylation or acylation.

The compounds of general formula (I) obtained by processes (a) and (b) can, if desired, be subsequently reacted with pharmacologically compatible acids or, when $R_3$ is a carboxyl radical, with non-toxic bases, to give the corresponding salts.

The reaction of 3-nitro-4-formyl-pyrazoles of the general formula (II) with compounds of the general formula (III) takes place according to generally known methods, advantageously in an inert organic solvent, for example pyridine, possibly in the presence of a little piperidine, and at an elevated temperature. When X in general formula (III) represents a hydrogen atom, there can also be used reactive derivatives of compounds of general formula (III), for example a carboxylic acid anhydride.

3-Amino-pyrazole derivatives of general formula (IV) are converted into the nitro compounds of general formula (I) in the usual manner, preferably by reaction with an alkali metal nitrite, for example sodium or potassium nitrite, and a mineral acid in the presence of copper powder as catalyst at a temperature of from $-10°$ to $+30°$ C., via the corresponding diazonium salt.

The subsequent conversion of a substituent $R_3$ into a different substituent $R_3$ can be carried out in the usual manner by saponification, esterification, transesterification, amidation, transamidation, dehydration, alkylation or acylation.

Thus, for example, a compound in which $R_3$ is a cyano group can be subsequently saponified in the usual manner to give the corresponding carboxylic acid of general formula (I) in which $R_3$ is a carboxyl radical. This reaction is preferably carried out with a strong acid, for example, concentrated hydrochloric acid, or with an aqueous solution of an alkali metal hydroxide, for example a 20% aqueous solution of sodium hydroxide. By the choice of suitable reaction conditions, it is possible to hydrolyse the nitrile group to the carboxylic acid amide stage, for example, with 98% sulphuric acid or with an aqueous, alkaline solution of hydrogen peroxide.

On the other hand, if desired, a carboxylic acid amide of the general formula (I) can be subsequently converted in known manner into the corresponding nitrile ($R_3$ in general formula (I)=CN), for example, by treatment with phosphorus oxychloride at an elevated temperature. Furthermore, it is possible to convert a carboxylic acid ester of general formula (I) ($R_3$=alkoxycarbonyl) into the corresponding carboxylic acid ($R_3$=carboxyl), by saponification. This saponification is carried out in the usual way, preferably by treatment of the carboxylic acid ester with a dilute aqueous solution of an alkali metal hydroxide at an elevated temperature.

On the other hand, a carboxylic acid of general formula (I) ($R_3$=carboxyl) can be esterfied in the usual manner to give the corresponding alkoxycarbonyl compound, for example by reaction with a lower alcohol and preferably with methanol or ethanol, in the presence of a hydrogen halide.

The conversion of a carboxyl group into an ester function can also take place in two stages by first converting the carboxylic acid in the usual manner into a reactive carboxylic acid derivative, for example, into a carboxylic acid chloride, and subsequently reacting this with a lower alcohol, preferably with methanol or ethanol, or with a corresponding alkali metal alcoholate, preferably a sodium or potassium alcoholate, to give the desired carboxylic acid ester of general formula (I).

Furthermore, it is possible to convert an alkoxycarbonyl compound of general formula (I) into an alkoxycarbonyl compound of general formula (I) with a different alkoxy radical by reaction with an appropriate lower alcohol, in known manner, preferably in the presence of an acid or base as catalyst.

The conversion of a compound of general formula (I), in which $R_3$ is a carboxyl group, into a corresponding carboxylic acid amide of general formula (I) ($R_3$=—CO-NR$_4$R$_5$) which it may possibly be desired to carry out, is generally carried out in known manner, for example, by reaction of a carboxylic acid or of a carboxylic acid ester of general formula (I) with ammonia or a substitution product thereof. However, here, too, it is especially preferred first to convert the carboxylic acid in known manner into a reactive derivative, for example into a carboxylic acid chloride, and then to react this with ammonia or with a substituted derivative thereof to give the desired carboxylic acid amides of general formula (I). This last reaction step can be carried out in the usual manner, preferably in the presence of an inert organic solvent, for example, pyridine, dioxan or toluene, possibly in admixture with water, and, depending upon the reactivity of the reaction components, at a temperature of from −20° to +200° C.

One form of subsequent N-alkylation is the reaction of a primary or secondary amide of general formula (I) by the Mannich reaction with a secondary amine, for example, pyrrolidine, piperidine or dialkylamines, in the presence of formaldehyde and usually in an aqueous organic phase, at an elevated temperature, N',N'-disubstituted N-aminomethyl-carboxylic acid amides of general formula (I) thereby being formed.

When an amino group is present in the substituent $R_4$, it can, if desired, be subsequently acylated in known manner with a conventional acylation agent, for example, a carboxylic acid chloride or carboxylic acid anhydride.

Furthermore, it is possible to convert a carboxylic acid amide of general formula (1 ($R_3$=—CO—NR$_4$R$_5$; $R_4$=R$_5$=H), via the corresponding carbonyl isocyanate, into an N-carbamoyl-carboxylic acid amide of general formula (1) ($R_3$=—CO-NR$_4$R$_5$; $R_4$=carbamoyl, alkylcarbamoyl or dialkylcarbamoyl; $R_5$=H). The conversion of a carboxylic acid amide into a carbonyl isocyanate is carried out in the usual manner, preferably by reaction of the carboxylic acid amide with oxalyl chloride in an inert organic solvent, for example chlorobenzene, at an elevated temperature. By the addition of ammonia or of an alkylamine or dialkylamine to the carbonyl isocyanate obtained, there is formed, in known manner, the desired carboxylic acid ureide derivative of general formula (I).

The starting compounds of general formula (II) can be obtained by converting 3-amino-4-alkoxycarbonylpyrazole derivatives (cf. Helv. Chim. Acta, 42, 349/1959) into the corresponding 3-nitro compounds, for example with an alkali metal nitrite and a mineral acid in the presence of copper powder, the carboxylic acid ester function being saponified, if desired, in known manner to give the free carboxylic acid group. The 3-nitro-4-carboxyl-pyrazole or 3-nitro-4-alkoxycarbonyl-pyrazole derivatives obtained can then be converted by known methods into the aldehyde compounds of general formula (II).

Thus, for example, it is possible to convert an appropriately substituted 3-nitropyrazole-4-carboxylic acid into the corresponding carboxylic acid chloride, to reduce this, for example, with lithium aluminium tri-tert.-butoxy hydride, at a low temperature to give a mixture of a 3-nitropyrazole-4-aldehyde and of a 3-nitro-4-hydroxymethyl-pyrazole derivative and to treat this mixture with an appropriate oxidation agent, preferably lead tetraacetate, in order also to convert its hydroxymethyl component into the desired aldehyde of general formula (II). The free 3-nitropyrazole-4-carboxylic acid or a corresponding ester can also be completely reduced to a 3-nitro-4-hydroxymethyl-pyrazole derivative, for example with sodium borohydride, with or without anhydrous aluminium chloride, and subsequently oxidised with, for example, lead tetraacetate, to give a 3-nitropyrazole-4-aldehyde compound of general formula (II).

The starting compounds of general formula (IV) can be prepared by converting a 3-amino-4-alkoxycarbonyl-pyrazole derivative (cf. Helv. Chim. Acta, 42, 349/1959) to the corresponding 3-aminopyrazole-4-aldehyde derivative. In principle, this can take place in the same manner as described above for the analogous 3-nitro compounds. The 3-aminopyrazole-4-aldehyde derivatives obtained can then be reacted in known manner with malonic acid or with a derivative thereof in a manner analogous to process variant (a) to give the desired 3-aminopyrazole-4-acrylic acid derivatives of general formula (IV).

For the conversion of compounds of general formula (I) into pharmacologically compatible salts, the compounds are reacted in the usual manner, preferably in an organic solvent, with an equivalent amount of a non-toxic inorganic or organic acid, for example, hydrochloric acid, hydrobromic acid, phosphoric acid, sulphuric acid, acetic acid, citric acid, lactic acid, malic acid, salicylic acid, malonic acid, maleic acid, succinic acid or benzoic acid or, when $R_3$ is a carboxyl radical, with an equivalent amount of a non-toxic inorganic or organic base.

For the preparation of pharmaceutical compositions, the compounds (I) are mixed in the usual manner with appropriate pharmaceutical carrier materials, aroma, flavoring or coloring materials and formed, for example, into tablets or dragees or, with the addition of appropriate adjuvants, suspended or dissolved in water or in an oil, for example, olive oil.

The compounds of general formula (I) according to the present invention and the salts thereof can be administered enterally or parenterally in liquid or solid form. This injection medium, it is preferable to use water which contains the additives usual in the case of injection solutions, such as stabilising agents, solubilising agents or buffers. Additives of this type include, for example, tartrate and citrate buffers, ethanol, complex-forming agents (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly-dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening materials.

Apart from the compounds specifically mentioned in the following Examples, the following compounds are also preferred according to the present invention:
3-(1-methyl-3-nitro-4-pyrazolyl)-acrylic acid N-isopropylamide; m.p. 189°–192° C.;
3-(1-methyl-3-nitro-4-pyrazolyl)-acrylic acid N-cyanomethylamide; m.p. 172°–174° C.;
3-(1-methyl-3-nitro-4-pyrazolyl)-acrylic acid N-acetylaminoethylamide; m.p. 246°–249° C.;
3-(1-methyl-3-nitro-4-pyrazolyl)-acrylic acid thioureide; m.p. 211°–212° C.
3-(1-methyl-3-nitro-4-pyrazolyl)-acrylic acid semicarbazide;
3-(1-methyl-3-nitro-4-pyrazolyl)-acrylic acid N-piperidinomethylamide; m.p. 185°–186°).;
3-(1-methyl-3-nitro-4-pyrazolyl)-acrylic acid N-aminoethylamide;
3-(1-methyl-3-nitro-4-pyrazolyl)-acrylic acid N-(N'-methylcarbamoyl)-amide; m.p. 257°–258° C.;
3-(1-methyl-3-nitro-4-pyrazolyl)-acrylic acid N',N'-dimethylureide; m.p. 174°–176° C.; and
3-(1-methyl-3-nitro-4-pyrazolyl)-acrylic acid N-methyl-N-aminoethylamide.

The following Examples are given for the purpose of illustrating the present invention:

EXAMPLE 1

3-(1-Methyl-3-nitro-4-pyrazolyl)-acrylic acid 6.3 g. 1-methyl-3-nitropyrazole-4-aldehyde are stirred with 4.45 g. malonic acid and 2 ml. pyridine for 30 minutes at 100° C. The reaction mixture is cooled and the mass obtained is triturated with isopropanol, filtered off with suction and washed with isopropanol and diethyl ether. The crystals obtained are then triturated with water and thereafter filtered off with suction and dried at 80° C. in a vacuum. There are obtained 4.86 g. 3-(1-methyl-3-nitro-4-pyrazolyl)-acrylic acid; m.p. 222°–223° C.

In an analogous manner from 1,5-dimethyl-3-nitropyrazole-4-aldehyde there is obtained 3-(1,5-dimethyl-3-nitro-4-pyrazolyl)-acrylic acid; m.p. 192°–194° C.

The 1-methyl-3-nitropyrazole-4-aldehyde used as starting material is prepared in the following manner:

(a) 1-Methyl-3-nitropyrazole-4-carboxylic acid 1.55 g. 1-methyl-3-amino-4-carbomethoxypyrazole (see Helv. Chim. Acta, 42, 349/1959) are dissolved in 8.8 ml. 35 hydrofluoboric acid and 10 ml. water. This solution is poured into a solution, with a temperature of 5° C., which contains 10 g. sodium nitrite in 50 ml. water, as well as 1 g. copper powder. The reaction mixture is stirred for 2 hours at ambient temperature and filtered and the residue is washed with ethyl acetate. The combined filtrates are extracted with ethyl acetate and the extract is dried and evaporated. The residue (1.65 g.) is stirred for 30 minutes in 16.5 ml. 2 N aqueous sodium hydroxide solution at 100° C. The reaction mixture is then cooled and filtered and the filtrate is acidified with 6 N hydrochloric acid. After filtering off the precipitate with suction, washing with water and drying, there is obtained 0.7 g. 1-methyl-3-nitropyrazole-4-carboxylic acid; m.p. 186°–188° C.

(b) 1-Methyl-3-nitropyrazole-4-aldehyde

Variant I:

15 g. 1-methyl-3-nitropyrazole-4-carboxylic acid are boiled under reflux for 1 hour with 150 ml. thionyl chloride. The solution obtained is evaporated in a vacuum and the residue obtained is triturated with 60 ml. petroleum ether to give 16 g. 1-methyl-3-nitropyrazole-4-carboxylic acid chloride; m.p. 68°–70° C.

14.6 g. of this acid chloride are dissolved in 155 ml. 1,2-dimethoxyethane, 20 g. lithium aluminium tri-tert.-butoxy hydride are introduced portionwise at −60° to −70° C. in the course of 45 minutes and the reaction mixture is then stirred for 1 hour, the temperature thereby being allowed to increase slowly to 0° C., whereafter the reaction mixture is poured into 0.5 liters of ice-water. The precipitate obtained is filtered off with suction and the clear filtrate is saturated with sodium chloride and extracted three times with ethyl acetate. The combined extracts are washed with an aqueous solution of sodium bicarbonate, dried in a vacuum and evaporated. There are obtained 5 g. of evaporation residue which, according to the thin layer chromatogram, consists of about equal parts of 1-methyl-3-nitropyrazole-4-aldehyde and 1-methyl-3-nitro-4-hydroxymethyl-pyrazole.

This mixture is dissolved in 250 ml. hot toluene, 25 g. lead tetraacetate are added thereto portionwise, while stirring, and the reaction mixture is subsequently boiled under reflux for 1 hour. A further 5 g. lead tetraacetate are then added and the reaction mixture is further boiled under reflux for 1 hour, cooled and the lead salt then filtered off with suction. The toluene filtrate is shaken up with a saturated aqueous solution of sodium carbonate, undissolved material is filtered off with suction and the organic phase in the filtrate is separated off. After drying and evaporating the toluene solution, there are obtained 4.85 g. 1-methyl-3-nitropyrazole-4-aldehyde which, according to the thin layer chromatogram, is practically uniform.

Variant II:

0.52 g. 1-methyl-3-nitropyrazole-4-carboxylic acid is introduced portionwise, while stirring, into a solution of 0.11 g. sodium borohydride in 3 ml. anhydrous diethylene glycol dimethyl ether, the temperature thereby increasing to about 45° C. A solution of 0.13 g. anhydrous aluminium chloride in 5 ml. anhydrous diethylene glycol dimethyl ether is now added slowly thereto, the reaction mixture is stirred for 1 hour at ambient temperature and for 1 hour at 60°–65° C., a further 0.05 g. sodium borohydride and 0.06 g. anhydrous aluminium trichloride are added thereto and the reaction mixture again stirred for 1 hour at 60°–65° C.

The reaction mixture is now cooled, poured on to crushed ice, to which some concentrated hydrochloric acid has been added, and extracted three times with ethyl acetate. The combined extracts are dried, evaporated in a vacuum at a bath temperature of 70° C. and the evaporation residue is triturated with petroleum ether. There is thus obtained 0.45 g. crude 1-methyl-3-nitro-4-hydroxymethyl-pyrazole which, after treatment with a little aqueous sodium bicarbonate solution, filtering with suction and washing with water, melts at 150°–152° C.

Alternatively, 12 g. 1-methyl-3-nitropyrazole-4-carboxylic acid in 300 ml. ethanol saturated with gaseous hydrogen chloride can be left to stand for 12 hours at ambient temperature and the reaction mixture then worked up to give 13.3 g. ethyl 1-methyl-3-nitropyrazole-4-carboxylate; m.p. 69°–71° C.

7.62 g. of this ester are added, with stirring, to a suspension of 1.35 g. sodium borohydride in 63 ml. 1,2-dimethoxyethane. To this is added portionwise, while stirring, 1.6 g. aluminium chloride, the temperature not being allowed to rise above 50° C., followed by stirring for 2 hours at 65° C. After a further addition of 0.34 g. sodium borohydride and 0.4 g. aluminium chloride and further stirring for 1.5 hours at 65° C., the suspension is evaporated in a vacuum at a bath temperature of 50° C. The evaporation residue is suspended in about 50 ml. water, the pH is adjusted to about 1 with concentrated hydrochloric acid, filtered with suction, washed with water and dried to give 4.96 g. 1-methyl-3-nitro-4-hydroxymethyl-pyrazole; m.p. 150°–153° C.

1.57 g. of the 1-methyl-3-nitro-4-hydroxymethyl-pyrazole thus obtained in 75 ml. hot toluene is mixed, while stirring, with 6.65 g. lead tetraacetate, followed by stirring for 1.5 to 2 hours under reflux. After cooling, the lead salt is filtered off with suction, the filtrate is shaken up with 2 N aqueous sodium carbonate solution and the organic phase is separated off, dried and evaporated in a vacuum to give 1.46 g. 1-methyl-3-nitropyrazole-4-aldehyde. After trituration with a little isopropanol and washing with isopropanol and diethyl ether, the melting point is 81°–83° C. The yield of purified product is then 0.85 g.

EXAMPLE 2

3-(1-Methyl-3-nitro-4-pyrazolyl)-acrylic acid ureide 2 g. 3-(1-methyl-3-nitro-4-pyrazolyl)-acrylic acid (preparation see Example 1) are stirred under reflux for 1 hour with 24 ml. oxalyl chloride, whereafter the solution is evaporated in a vacuum. Some petroleum ether is added to the evaporation residue, followed by evaporating again and this latter process is repeated once more in order completely to remove oxalyl chloride and hydrochloric acid. There are thus obtained 2.19 g. crude 3-(1-methyl-3-nitro-4-pyrazolyl)-acrylic acid chloride; m.p. 84°–86° C.

To a suspension of 0.46 g. urea in 14 ml. pure pyridine, there is added dropwise, within the course of 15 minutes, while stirring at 50° C., a solution of 1.5 g. of this crude 3-(1-methyl-3-nitro-4-pyrazolyl)-acrylic acid chloride in 14 ml. dry dioxan, followed by stirring for 2 hours at 50° C. The reaction mixture is then cooled to ambient temperature, filtered with suction to remove undissolved material, washed with dioxan and diethyl ether and the product thus obtained (1.5 g.) triturated with 3 ml. water. It is now filtered off with suction, washed with water and diethyl ether and dried to give 0.95 g. 3-(1-methyl-3-nitro-4-pyrazolyl)-acrylic acid ureide; m.p. 244°–246° C. (with foaming).

EXAMPLE 3

3-(1-Methyl-3-nitro-4-pyrazolyl)-acrylamide

From 1.26 g. 3-(1-methyl-3-nitro-4-pyrazolyl)-acrylic acid (preparation see Example 1) and 15 ml. oxalyl chloride, there is prepared, in the manner described in Example 2, the corresponding acrylic acid chloride and this is dissolved in 45 ml. pure toluene. Dry ammonia gas is passed into this solution for 15 minutes at 15°–20° C.; while stirring. The precipitated crystals are filtered off with suction, washed with toluene and, after drying, triturated with water. The product is again filtered off with suction, washed with water and ethanol and dried in a vacuum at 110° C. There is thus obtained 1.17 g. 3-(1-methyl-3-nitro-4-pyraolyl)-acrylamide; m.p. 255°–257° C. (change above 248° C.). The product still contains about ⅓ mol water.

In an analogous manner, from 3-(1,5-dimethyl-3-nitro-4-pyrasolyl)-acrylic acid, there is obtained, via its acid chloride and ammonia gas, 3-(1,5-dimethyl-3-nitro-4-pyrazolyl)-acrylamide; m.p. 225°–229° C.

EXAMPLE 4

3-(1-Methyl-3-nitro-4-pyrazolyl)-N-hydroxyacrylamide 8.12 g. hydroxylamine hydrochloride are dissolved in 100 ml. methanol, and 9.35 g. sodium hydroxide in 140 ml. methanol added thereto. The precipitated sodium chloride is separated off and the solution is made up to 250 ml. with methanol. 12.5 ml. of this solution (containing 0.193 g. hydroxylamine) are mixed portionwise at 0° C. with 0.54 g. 3-(1-methyl-3-nitro-4-pyrazolyl)-acrylic acid chloride (preparation see Example 2) and thoroughly stirred for 15 minutes at 0° C. The temperature is then allowed to increase to ambient temperature and solid material is filtered off with suction and washed with methanol. The yellow-brown substance thus obtained is suspended in about 3 ml. water and well acidified with 2 N hydrochloric acid. The beige-coloured substance obtained is filtered off with suction, washed with water and dried in a vacuum. There is thus obtained 0.36 g. 3-(1-methyl-3-nitro-4-pyrazolyl)-N-hydroxyacrylamide; m.p. 172°–174° C. (with foaming). 0.1 g. of this substance is recrystallised from 2 ml. of a dioxan-water mixture (9:1), with the addition of active charcoal. The recrystallised product has a melting point of 183°–184° C.

EXAMPLE 5

3-(1-Methyl-3-nitro-4-pyrazolyl)-acrylic acid N-(β-hydroxyethyl)-amide

Into a solution of 0.6 g. β-hydroxyethylamine in 12 ml. methanol, there is introduced portionwise at 0° C., 0.65 g. 3-(1-methyl-3-nitro-4-pyrazolyl)-acrylic acid chloride (preparation see Example 2). The reaction mixture is stirred for 10 minutes at 0° C. and thereafter for 30 minutes at ambient temperature. The solid material is then filtered off with suction and washed with methanol and diethyl ether to give 0.42 g. 3-(1-methyl-3-nitro-4-pyrazolyl)-acrylic acid N-(β-hydroxyethyl)-amide; m.p. 176°–178° C. (with foaming).

EXAMPLE 6

3-(1-Methyl-3-nitro-4-pyrazolyl)-acrylic acid thiosemicarbazide

To a suspension of 0.3 g. thiosemicarbazide in 6 ml. anhydrous pyridine is added dropwise at 2°–3° C., in the course of 45 minutes, a solution of 0.65 g. 3-(1-methyl-3-nitro-4-pyrazolyl)-acrylic acid chloride (preparation see Example 2) in 6 ml. dioxan. The reaction mixture is stirred for 1 hour at 2°–3° C. and for 1 hour at ambient temperature. The suspension is then evaporated in a vacuum and the solid residue triturated with 1 N hydrochloric acid. After filtering with suction and washing with water, there is obtained 0.68 g. 3-(1-methyl-3-nitro-4-pyrazolyl)-acrylic acid thiosemicarbazide; m.p. 208°–210° C. (with foaming).

EXAMPLE 7

3-(1-Ethyl-3-nitro-4-pyrazolyl)-acrylic acid 20 g. 3-nitro-4-pyrazole-carbonitrile are stirred with 17.5 ml. ethyl iodide, 21 g. potassium carbonate and 145 ml. 1,2-dimethoxyethane for 2 hours under reflux, followed by cooling. The inorganic material is then filtered off with suction. The filtrate is evaporated in a vacuum, the evaporation residue is dissolved in about 250 ml. ethyl acetate and this solution is shaken up with 150 ml. aqueous 2 N potassium carbonate solution and with sodium thiosulphate solution. The organic phase is separated off, dried and evaporated in a vacuum to give 21.7 g. crude 1-ethyl-3-nitro-4-pyrazole carbonitrile in the form of an oil.

15.7 g. 1-ethyl-3-nitro-4-pyrazole carbonitrile are introduced into a solution of 15.7 g. solid sodium hydroxide in 170 ml. water and stirred under reflux for 1 hour, the oil thereby slowly going into solution. After cooling, it is well acidified with concentrated hydrochloric acid and the precipitated crystals are filtered off with suction, washed with water and dried. There are thus obtained 12.45 g. crude 1-ethyl-3-nitropyrazole-4-carboxylic acid; m.p. 160°–163° C. (change from 155° C.).

9.25 g. of this acid are stirred for 1 hour under reflux with 90 ml. thionyl chloride. The solution is then evaporated in a vacuum, petroleum ether is added thereto and the mixture again evaporated. The oily evaporation residue (crude 1-ethyl-3-nitropyrazole-4-carboxylic acid chloride) is now dissolved in 30 ml. anhydrous 1,2-dimethoxyethane and, while stirring at −60° to −70° C., a solution of 12.8 g. lithium aluminium tri-tert.-butoxy hydride in 50 ml. anhydrous dimethoxyethane is added dropwise over the course of 45 minutes. The reaction mixture is thereafter stirred for 1 hour, the temperature being allowed to increase slowly to 0° C. 250 ml. ice water are now poured in, the precipitate is filtered off with suction and the aqueous filtrate is saturated with sodium chloride and extracted three times with ethyl acetate. The combined extracts are shaken with 2 N aqueous sodium carbonate solution, the ethyl acetate phase is separated off and, after drying, evaporated in a vacuum, 3.15 g. of an oily residue remaining behind. According to the thin layer chromatogram, there is present a mixture of about equal parts of 1-ethyl-3-nitro-4-hydroxymethyl-pyrazole and 1-ethyl-3-nitropyrazole-4-aldehyde, which is further worked up without further purification.

This 3.15 g. of oily mixture are well mixed with 2.03 g. malonic acid and 0.95 ml. pyridine and heated to a bath temperature of 100° C., a vigorous evolution of gas thereby taking place. The reaction mass is kept for 30 minutes at 100° C., then cooled and triturated three times with diethyl ether and then with about 7 ml. of a water-isopropanol mixture (7:3). The crystals obtained are filtered off with suction and washed with a little isopropanol and diethyl ether. There is thus obtained 0.82 g. crude 3-(1-ethyl-3-nitro-4-pyrazolyl)-acrylic acid; m.p. 219°–220° C. (change above 191° C.).

EXAMPLE 8

3-(1-Ethyl-3-nitro-4-pyrazolyl)-acrylamide 0.82 g. 3-(1-ethyl-3-nitro-4-pyrazolyl)-acrylic acid is stirred with 10 ml. oxalyl chloride for 1 hour under reflux. The solution is then evaporated in a vacuum and petroleum ether is added thereto, followed by evaporating again. The latter procedure is preferably repeated in order to remove oxalyl chloride and hydrochloric acid as completely as possible. The oily evaporation residue is crude 3-(1-ethyl-3-nitro-4-pyrazolyl)-acrylic acid chloride. This is dissolved in 30 ml. anhydrous toluene and, while stirring, ammonia gas is passed in for 15 minutes at 15°–20° C. The product which thereby precipitates out is filtered off with suction, washed with toluene and dried. The crystals thus obtained are thoroughly triturated with water, filtered off with suction, washed with water and ethanol and finally dried in a vacuum at 100° C. There is thus obtained 0.75 g. 3-(1-ethyl-3-nitro-4-pyrazolyl)-acrylamide; m.p. 210°–212° C. (change above 203° C.).

EXAMPLE 9

Methyl 3-(1-methyl-3-nitro-4-pyrazolyl)-acrylate 1.3 g. of the 3-(1-methyl-3-nitro-4-pyrazolyl)-acrylic acid described in Example 1 is dissolved in 52 ml. warm methanol and the solution saturated at ambient temperature with gaseous hydrogen chloride and thereafter left to stand overnight. The reaction solution is then evaporated in a vacuum at ambient temperature (bath temperature) and the evaporation residue is triturated with a saturated aqueous solution of sodium dicarbonate, filtered off with suction and washed with water to give 1 g. methyl 3-(1-methyl-3-nitro-4-pyrazolyl)-acrylate; m.p. 110°–112° C.

The same product is obtained when 0.22 g. of the 3-(1-methyl-3-nitro-4-pyrazolyl)-acrylic acid chloride described in Example 2 is allowed to react in 1.8 ml. methanol for 30 minutes at ambient temperature and the resultant crystals filtered off with suction.

EXAMPLE 10

3-(1-Methyl-3-nitro-4-pyrazolyl)-acrylic acid N-(6-methyl-2-pyridyl)-amide 0.215 g. 3-(1-methyl-3-nitro-4-pyrazolyl)-acrylic acid chloride (preparation see Example 2) is dissolved in 3 ml. dioxan and mixed at ambient temperature, while stirring, with 2-amino-6-methylpyridine. After a short time, crystals begin to precipitate out. Stirring is continued for 30 minutes at ambient temperature, followed by dilution with water. The solid is filtered off with suction and then washed with water. After drying, there is obtained 0.23 g. 3-(1-methyl-3-nitro-4-pyrazolyl)-acrylic acid N-(6-methyl-2-pyridyl)-amide; m.p. 191°–193° C.

EXAMPLE 11

3-(1-Methyl-3-nitro-4-pyrazolyl)-acrylic acid N-methylamide 0.54 g. 3-(1-methyl-3-nitro-4-pyrazolyl)-acrylic acid chloride (preparation see Example 2) is dissolved in 20 ml. anhydrous toluene and, while stirring at 25° C., methylamine gas is passed in for about 10 minutes. The precipitated crystals are filtered off with suction, washed with toluene, triturated with water and dried in a vacuum. There is thus obtained 0.43 g. 3-(1-methyl-3-nitro-4-pyrazolyl)-acrylic acid N-methylamide; m.p. 200°–203° C.

EXAMPLE 12

3-(1-Methyl-3-nitro-4-pyrazolyl)-acrylic acid N-(4-hydroxyphenyl)-amide 0.43 g. 3-(1-methyl-3-nitro-4-pyrazolyl)-acrylic acid chloride (preparation see Example 2) is dissolved in 6 ml. dioxan and 0.64 g. 4-hydroxyaniline is added thereto, while stirring, stirring being continued for 30 minutes at ambient temperature. The precipitated crystals are filtered off with suction and washed with dioxan and then with water. After drying in a vacuum at 100° C., there is obtained 0.58 g. 3-(1-methyl-3-nitro-4-pyrazolyl)-acrylic acid N-(4-hydroxyphenyl)-amide; m.p. 290°–293° C. (with foaming).

EXAMPLE 13

3-(1-Methyl-3-nitro-4-pyrazolyl)-acrylic acid N-(pyrrolidinomethyl)-amide 1 g. 3-(1-methyl-3-nitro-4-pyrazolyl)-acrylamide (preparation see Example 3) is mixed with 3.5 ml. methanol, 1 ml. pyrrolidine and 0.9 ml. 37% aqueous formaldehyde solution and stirred under reflux for 4 hours. A further 1 ml. pyrrolidine and 0.9 ml. formaldehyde solution are added thereto and the reaction mixture is kept under reflux for a further 3 hours. 1 ml. pyrrolidine and 0.9 ml. formaldehyde are again added thereto and stirring under reflux continued for a further 6 hours. The reaction mixture is then completely evaporated to dryness in a vacuum, the residue is triturated with methanol and the solid material is filtered off with suction. There is thus obtained 0.34 g. 3-(1-methyl-3-nitro-4-pyrazolyl)-acrylic acid N-(pyrrolidinomethyl)-amide; m.p. 180°–183° C. It is soluble in dilute hydrochloric acid. A further 0.35 g. of the same compound is obtained from the mother liquor by evaporation.

EXAMPLE 14

3-(1-Methyl-3-nitro-4-pyrazolyl)-acrylic acid N-allylamide 1.1 g. 3-(1-methyl-3-nitro-4-pyrazolyl)-acrylic acid chloride (preparation see Example 2) is dissolved in 15 ml. pure dioxan and 1.14 ml. allylamine added thereto, while stirring, the temperature thereby increasing to about 45° C. and an oil separates out. The reaction mixture is evaporated in a vacuum, the residue is triturated with water and the crystals obtained are filtered off with suction. After washing with water and drying in a vacuum at 100° C., there is obtained 0.94 g. 3-(1-methyl-3-nitro-4-pyrazolyl)-acrylic acid N-allylamide; m.p. 143°–146° C.

EXAMPLE 15

3-(1-Methyl-3-nitro-4-pyrazolyl)-acrylic acid N-cyclopropylamide 0.645 g. 3-(1-methyl-3-nitro-4-pyrazolyl)-acrylic acid chloride (preparation see Example 2) is dissolved in 6 ml. anhydrous dioxan and 0.513 g. cyclopropylamine added thereto, while stirring and cooling. The reaction mixture is further stirred for 30 minutes at ambient temperature and the precipitated substance (0.72 g.) is filtered off with suction and triturated with water to give 0.6 g. 3-(1-methyl-3-nitro-4-pyrazolyl)-acrylic acid N-cyclopropylamide; m.p. 183°–185° C. (with foaming) in the form of bright yellow crystals.

In an analogous manner, from 3-(1-methyl-3-nitro-4-pyrazolyl)-acrylic acid chloride, there is obtained by reaction with a. piperidine, 3-(1-methyl-3-nitro-4-pyrazolyl)-acrylic acid piperidine; m.p. 190°–191° C.;
b. N,N-diethylethylenediamine, 3-(1-methyl-3-nitro-4-pyrazolyl)-acrylic acid N-diethylaminoethylamide; m.p. 109°–110° C.

EXAMPLE 16

Methyl 3-(1-methyl-3-nitro-4-pyrazolyl)-acrylate 0.5 g. 1-methyl-3-nitro-pyrazole-4-aldehyde and 0.85 g. monomethyl malonate are stirred in 1.6 ml. pyridine and 0.04 ml. piperidine for 2 hours at 100° C. The reaction mixture is then cooled, poured on to ice and acidified with dilute hydrochloric acid. The suspension is filtered off with suction and washed with water until neutral. After drying, there is obtained 0.45 g. (66% of theory) of the desired methyl 3-(1-methyl-3-nitro-4-pyrazolyl)-acrylate; m.p. 110°–112° C. The mixed melting point with the product obtained in Example 9 shows no depression.

EXAMPLE 17

3-(1-Methyl-3-nitro-4-pyrazolyl)-acrylamide 0.5 g. 1-methyl-3-nitropyrazole-4-aldehyde and 0.65 g. malonic acid monoamide are dissolved in 1.6 ml. pyridine, mixed with 1 drop of piperidine and stirred for 1.75 hours at 100° C. The reaction mixture is then cooled and poured on to ice and the suspension is filtered off with suction. It is thoroughly washed with water and dried to give 0.25 g. (40% of theory) of the desired 3-(1-methyl-3-nitro-4-pyrazolyl)-acrylamide.

When the reaction of 1-methyl-3-nitropyrazole-4-aldehyde and malonic acid monoamide in pyridine is carried out at 70° C., then, as intermediate product, there can be isolated 2-carbamoyl-3-(1-methyl-3-nitro-4-pyrazolyl)-acrylic acid. For decarboxylation, 0.1 g. of this product is stirred in 1 ml. pyridine for 1.5 hours at a bath temperature of 120° C. The reaction mixture is then cooled, ice-cold semi-concentrated hydrochloric acid is added thereto and the precipitated crystals are filtered off with suction, washed with water and dried. There is obtained 0.02 g. 3-(1-methyl-3-nitropyrazolyl)-acrylamide.

The mixed melting point with the product obtained in Example 3 shows no depression.

The 1-methyl-3-nitropyrazole-4-aldehyde used as starting material is obtained as follows:

0.97 g. 3-(5)-amino-4-methylpyrazole (see Chem. Abs., 59, 5147/1963) is dissolved in 8.8 ml. 35% hydrofluoboric acid and 10 ml. water. This solution is poured into a solution, with a temperature of 5° C., which contains 10 g. sodium nitrite in 50 ml. water, as well as 1 g. copper powder. The reaction mixture is thereafter stirred for 2 hours at ambient temperature, filtered and the residue washed with ethyl acetate. The combined filtrates are extracted with ethyl acetate and the extract is dried and evaporated. The residue is taken up in diethyl ether, filtered and again evaporated. There is thus obtained 0.35 g. (28% of theory) semi-crystalline 3-(5)-nitro-4-methylpyrazole.

1.4 g. of this compound is stirred under reflux for 4.5 hours with 1.8 ml. methyl iodide and 1.6 g. potassium carbonate in 11.4 ml. ethylene glycol dimethyl ether. The reaction mixture is then cooled, filtered and the filtrate evaporated in a vacuum. The residue is taken up in ethyl acetate, successively washed with aqueous potassium carbonate solution, aqueous sodium thiosulphate solution and finally with water, then dried and evaporated. There is then obtained 1.15 g. (74% of theory) semi-crystalline 1,4-dimethyl-3-nitropyrazole.

This is dissolved in 25 ml. of a mixture of equal parts by volume of acetic acid and acetic anhydride. 1.9 ml. concentrated sulphuric acid is then added dropwise and 2.2 g. chromium trioxide are added thereto portionwise. By means of occasional cooling, a temperature increase above 40° C. as avoided. After further stirring for 2 hours at 50° C., the reaction mixture is poured on to ice, the pH value is adjusted to 7.5–8 by means of a concentrated aqueous solution of ammonia and the reaction mixture is then extracted with ethyl acetate. After drying and evaporating the extract, there is obtained 0.8 g. (38% of theory) oily 1-methyl-3-nitropyrazole-4-aldehyde diacetate, which is stirred with 8 ml. 6 N hydrochloric acid for 1 hour at 50° C. After cooling, the reaction mixture is extracted with ethyl acetate, dried and evaporated. There is thus obtained 0.45 g. (95% of theory) 1-methyl-3-nitropyrazole-4-aldehyde, which is identical with the product described in Example 1.

EXAMPLE 18

3-(1-Methyl-3-nitro-4-pyragolyl)-acrylonitrile

Variant A:

3.38 g. 3-(1-methyl-3-nitro-4-pyrazolyl)-acrylamide are stirred in 8.5 ml. phosphorus oxychloride for 2 hours at 125° C. The reaction mixture is then evaporated in a vacuum, cooled and the reaction neutralized with ice-cold aqueous ammonia solution. There are obtained 2.85 g. crude 3-(1-methyl-3-nitro-4-pyrazolyl)-acrylonitrile. After recrystallisation from methanol-dioxan, with the addition of active charcoal, there is obtained 1.45 g. (48% of theory) of pure compound; m.p. 146°–148° C.

Variant B:

1 g. 1-methyl-3-nitropyrazole-4-aldehyde and 0.66 g. cyanoacetic acid are stirred for 1 hour at 70° C. in 2 ml. pyridine and 0.06 ml. piperidine. The reaction mixture is then cooled and the reaction mixture is acidified, filtered off with suction, washed with water and dried. 0.1 g. of the product obtained is heated for 2.5 hours in 1 ml. pyridine at a bath temperature of 120° C., decarboxylation thereby taking place. Thereafter, ice-cold, semi-concentrated hydrochloric acid is added thereto, followed by extraction with ethyl acetate. Evaporation of the extract gives 0.03 g. of the desired 3-(1-methyl-3-nitro-4-pyrazolyl)-acrylonitrile; m.p. 146°–148° C. The mixed melting point with the product obtained according to Variant A shows no depression.

EXAMPLE 19

3-(1-Methyl-3-nitropyrazolyl)-acrylamide 0.1 g. of the 3-(1-methyl-3-nitro-4-pyrazolyl)-acrylonitrile prepared according to Example 18, Variant B, is dissolved in 1 ml. concentrated sulphuric acid and stirred for 1 hour at ambient temperature. After leaving the reaction mixture to stand overnight, ice is added thereto and the precipitated crystalline product is filtered off with suction, washed with water and dried. There is obtained 0.08 g. (73% of theory) of the desired 3-(1-methyl-3-nitropyrazolyl)-acrylamide. The mixed melting point with the product obtained according to Example 3 shows no depression.

EXAMPLE 20

Sodium 3-(1-methyl-3-nitro-4-pyrazolyl)-acrylate 197 mg. 3-(1-methyl-3-nitro-4-pyrazolyl)-acrylic acid (prepared according to Example 1) are neutralized with a dilute aqueous solution of sodium hydroxide. The clear solution is evaporated to dryness and the residue is triturated with isopropanol. After filtering off with suction and washing with diethyl ether, there are obtained 170 mg. of the desired sodium salt; m.p. 306° (with foaming).

The antimicrobial activity of the instantly disclosed compounds was confirmed by the testing of a number of representative or illustrative compounds in certain tests. In one series of test, the absolute bacteriostatic minimum concentration for each test compound was determined and expressed in micrograms per milliliter. Thus, Table I below sets forth, for each test compound, the maximum extent to which the test compound in question can be diluted and still exhibit bacteriostatic activity. As a comparison substance, there was used the commercial bacteriostat known as "Furadantin", which is identified chemically as N-(5-nitrofuryliden)-1-aminohydantoin. It will be seen from the data presented in Table I that the instantly claimed compounds are substantially more active as bacteriostats than the comparison compound, i.e., Furadantin, in that much lower concentrations of the test compounds were capable of acting bacteriostatically, relative to the higher dosages of Furadantin required to achieve this effect. The data for Furadantin are presented at the end of Table I infra.

The following were the test compounds of the invention:

Compound I = 3-(1-methyl-3-nitro-4-pyrazolyl)-acrylamide

Compound II = 3-(1-ethyl-3-nitro-4-pyrazolyl)-acrylamide

Compound III = 3-(1-methyl-3-nitro-4-pyrazolyl)-N-hydroxyacrylamide

Compound IV = 3-(1-methyl-3-nitro-4-pyrazolyl)-acrylic acid ureide

Compound V = 3-(1-methyl-3-nitro-4-pyrazolyl)-acrylic acid-N-(pyrrolidinomethyl)-amide Compound VI = 3-(1-methyl-3-nitro-4-pyrazolyl)-acrylic acid-N-methylamide Compound VII = 3-(1-methyl-3-nitro-4-pyrazolyl)-acrylic acid-N-cyclopropylamide Compound VIII = 3-(1-methyl-3-nitro-4-pyrazolyl)-acrylic acid-N-cyanomethylamide Compound IX = 3-(1-methyl-3-nitro-4-pyrazolyl)-acrylic acid-thioureide Compound X = 3-(1-methyl-3-nitro-4-pyrazolyl)-acrylic acid-N-piperidinomethylamide Compound XI = 3-(1-methyl-3-nitro-4-pyrazolyl)-acrylic acid-N',N'-dimethylureide Compound XII = 3-(1-methyl-3-nitro-4-pyrazolyl)-acrylic acid-N-(N'-methylcarbamoyl)-amide Compound XIII = 3-(1,5-dimethyl-3-nitro-4-pyrazolyl)-acrylamide Comparison Compound:
Furadantin = N-(5-nitrofuryliden)-1-amino-hydantoin.

TABLE I

Bacteriostatic Effect in Vitro
Absolute Bacteriostatic Minimum Concentration in ug/ml
Bacterio Type ( ) Strain

| Active Compound | Escherichia coli (108) | Escherichia Proteus coli (298) | monas mirabilis (71) | Pseudo-aeruginosa |
|---|---|---|---|---|
| Compound I | 0.25 | 0.125 | 128 | 64 |
| Compound II | 1 | 0.5 | | |
| Compound III | 4 | 4 | 256 | 64 |
| Compound IV | 1 | 0.5 | | |
| Compound V | 1 | 0.25 | | |
| Compound VI | 1 | 0.5 | | |
| Compound VII | 4 | 2 | | |
| Compound VIII | 2 | 2 | | |
| Compound IX | 1 | 1 | | |
| Compound X | 1 | 0.25 | | |
| Compound XI | 4 | 2 | 256 | 128 |
| Compound XII | 4 | 1 | 256 | 128 |
| Compound XIII | 1 | 0.5 | 256 | 256 |
| Furadantin | 4 | 4 | 256 | 128 |

In another series of tests, the bacteriostatic activity of certain illustrative compounds of this invention in urine was tested and the percentage of administered test substance excreted in the urine was was determined, after oral administration, in rats. Again, the comparison substance "Furadantin" (nitrofurantoin) was used in side-by-side comparisons. The results obtained are set forth in Table II below, in which the column headed "Maximal Dilution" represents the maximum extent to which the urine sample could be diluted and still exhibit bacteriostatic activity against the test bacterium, which was Escherichia Coli (106). The test compounds were administered at the rate of 40 mg and 20 mg of test compound per kg of the rat's body weight, and are on the basis of 75 ml of urine per 22 hours after oral administration of the test compound. Each test value is based on the averages of values obtained in tests in nine rats and in the instances where two or more values are set forth, two or more determinations were made. The corresponding value for the reference standard "Furadantin" is set forth at the bottom of Table II. It can be seen that the compounds representative of the instant invention were capable of being diluted to a substantially greater extent than Furadantin, and still exhibit bacteriostatic activity; also, most of the compounds of the invention were excreted in urine to a much greater extent than Furadantin.

TABLE II

Bacteriostatic Activity in Urine in Rats after Oral Administration

| Test Substance | Maximal Dilution 40 mg/kg | 20 mg/kg |
|---|---|---|
| 3-(1-methyl-3-nitro-4-pyrazolyl)-acrylamide | | 1 : 1707 |
| | | 1 : 1120 |
| | | 1 : 2880 |
| | | 1 : 1216 |
| 3-(1-ethyl-3-nitro-4-pyrazolyl)-acrylamide | | 1 : 427 |
| 3-(1-methyl-3-nitro-4-pyrazolyl)-N-hydroxyacrylamide | 1 : 960 | 1 : 768 |
| 3-(1-methyl-3-nitro-4-pyrazolyl)-acrylic acid-N-(β-hydroxyethyl)-amide | 1 : 235 | 1 : 111 |
| | | 1 : 168 |
| 3-(1,5-dimethyl-3-nitro-4-pyrazolyl)-acrylamide | 1 : 296 | 1 : 208 |
| | | 1 : 146 |
| 3-(1-methyl-3-nitro-4-pyrazolyl)-acrylic acid-N-(6-methyl-2-pyridyl)-amide | 1 : 43 | |
| | 1 : 39 | |
| 3-(1-methyl-3-nitro-4-pyrazolyl)-acrylic acid-N-(pyrrolidinomethyl)-amide | | 1 : 875 |
| 3-(1-methyl-3-nitro-4-pyrazolyl)-acrylic acid-N-methylamide | | 1 : 616 |
| 3-(1-methyl-3-nitro-4-pyrazolyl)-acrylic acid-N-allylamide | | 1 : 152 |
| 3-(1-methyl-3-nitro-4-pyrazolyl)-acrylic acid-N-cyclopropylamide | | 1 : 84 |
| 3-(1-methyl-nitro-4-pyrazolyl)-acrylic acid-piperidine | 1 : 120 | |
| 3-(1methyl-3-nitro-4-pyrazolyl)-acrylic acid-N-isopropylamide | 10 : 359 | 1 : 260 |
| 3-(1-methyl-3-nitro-4-pyrazoly)-acrylic acid-N-cyanomethylamide | | 1 : 270 |
| 3-(1-methyl-3-nitro-4-pyrazolyl)-acrylic acid-N-piperidinomethylamide | 1 : 348 | |
| 3-(1-methyl-3-nitro-4-pyrazolyl)-acrylic acid-N',N'-dimethylureide | 1 : 94 | |
| Furadantin | | 1 : 19 |
| | | 1 : 21 |

In another series of tests, the in vivo effectiveness of the inventive compounds in mice was determined, according to the following procedure.

Female mice (inbreeding strain NMRI), weight 19–21 g, were infected by injecting 0.5 ml of a diluted 18-hour bouillon culture of *Escherichia Coli* (1C8) intraperitoneally into the animals. The intensity of the infection was adjusted so that without treatment at least 95% of the animals died during the first two days. 40 animals were used for these infection controls.

Treatment:

The treatment took place directly after the infection in the form of a single subcutaneous dose. The volume of the single dosage amounted to 0.5 ml (substance dissolved in distilled water or 5% tylose mucus). 10 animals were used in each test at each dosage.

In each case, ten control animals were not infected but only treated with the two highest dosages of the test substances. These control tests served as a basis for determining the losses of animals caused by the test compound.

The animals were observed for four days, the number of the deceased animals being determined daily, and the survival rate after four days determined.

The results are set forth in Table III below.

TABLE III

| | In Vivo Tests in Mice | | | | |
|---|---|---|---|---|---|
| | % Surviving Animals | | | | |
| Test Compound | 320 mg/kg | 160 mg/kg | 80 mg/kg | 40 mg/kg | 20 mg/kg |
| Compound I | | | | | 100 |
| Compound II | | | | | 50 |
| Compound III | | | | | 50 |
| Compound V | | | | | 100 |
| Compound VIII | | | | | 10 |
| Comparison Substance: | | | | | |
| Penicillin G | 100 | 90 | 40 | 0 | |

The particular mode of administration and dosage of inventive compound to be applied in treating a given bacterial infection or infirmity will, of course, be determined by the physician, taking into account all the circumstances of a particular case. However, in general, tablets containing the test compound to be administered per os, will contain about 250 mg of active material and, for local administration, may contain about 500 mg of active substance. The dosage to be applied may be one tablet taken in the morning and in the evening with the corresponding meal, for, e.g., ten consecutive days, if the compound is applied per os. For local administration, one ovule may be applied for 10 to 20 days every evening. In men, the per os administration may have to be increased to, e.g., 750 mg to 1 g, instead of the standard 250 mg per tablet dosage.

In will be understood that the specification and examples are illustrative but not limitative of the present invention and that other embodiments within the spirit and scope of the invention will suggest themselves to those skilled in the art.

What is claimed is:

1. 3-Nitropyrazole compound of the formula

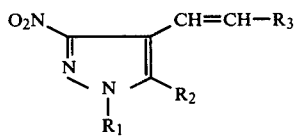

wherein
R$_1$ is lower alkyl;
R$_2$ is hydrogen or lower alkyl;
R$_3$ is the radical —CO—NR$_4$R$_5$, in which
R$_4$ is hydrogen or hydroxyl, carbamoyl, alkylcarbamoyl, dialkylcarbamoyl, thiocarbamoyl, ureido, thioureido, hydroxyphenyl, picolyl or is a lower alkyl, alkenyl or a cycloalkyl radical substituted, if desired, by a cyano, hydroxyl, pyrrolidino, piperidino, amino, lower alkylamino, lower dialkylamino or lower acylamino substituent and
R$_5$ is a hydrogen atom or a lower alkyl radical or
R$_4$ and R$_5$ together represent a lower alkylene bridge; and pharmaceutically acceptable salts thereof.

2. 3-Nitropyrazole compound as claimed in claim 1 wherein R$_1$ is alkyl of up to 5 carbon atoms.

3. 3-Nitropyrazole compound as claimed in claim 1 wherein R$_2$ is hydrogen.

4. 3-Nitropyrazole compound as claimed in claim 1 wherein R$_2$ is alkyl of up to 5 carbon atoms.

5. 3-Nitropyrazole compound as claimed in claim 1 wherein R$_5$ is hydrogen.

6. 3-Nitropyrazole compound as claimed in claim 1 wherein R$_4$ is hydrogen or hydroxy.

7. 3-Nitropyrazole compound as claimed in claim 1 wherein R$_4$ is carbamoyl, alkylcarbamoyl, dialkylcarbamoyl or thiocarbamoyl of up to 5 carbon atoms per alkyl moiety.

8. 3-Nitropyrazole compound as claimed in claim 1 wherein R$_4$ is ureido or thioureido.

9. 3-Nitropyrazole compound as claimed in claim 1 wherein R$_4$ is hydroxyphenyl.

10. 3-Nitropyrazole compound as claimed in claim 1 wherein R$_4$ is picolyl.

11. 3-Nitropyrazole compound as claimed in claim 1 wherein R$_4$ is alkyl, alkenyl or cycloalkyl.

12. 3-Nitropyrazole compound as claimed in claim 1 wherein R$_4$ is substituted alkyl, substituted alkenyl or substituted cycloalkyl wherein the substituents are selected from cyano, hydroxyl, pyrrolidino, piperidino, amino, lower alkylamino, lower dialkylamino and lower acylamino of up to 5 carbon atoms per alkyl moiety.

13. 3-Nitropyrazole compound as claimed in claim 1 wherein R$_5$ is hydrogen.

14. 3-Nitropyrazole compound as claimed in claim 1 wherein R$_5$ is lower alkyl.

15. 3-Nitropyrazole compound as claimed in claim 1 wherein R$_4$ and R$_5$ together represent alkylene of 4 or 5 carbon atoms.

16. 3-Nitropyrazole compound as claimed in claim 1 designated 3-(1-methyl-3-nitro-4-pyrazolyl)-acrylamide.

17. 3-Nitropyrazole compound as claimed in claim 1 designated 3-(1-methyl-3-nitro-4-pyrazolyl)-N-hydroxyacrylamide.

18. 3-Nitropyrazole compound as claimed in claim 1 designated 3-(1-ethyl-3-nitro-4-pyrazolyl)-acrylamide.

19. 3-Nitropyrazole compound as claimed in claim 1 designated 3-(1-methyl-3-nitro-4-pyrazolyl)-acrylic acid-N-methylamide.

20. 3-(1-methyl-3-nitro-4-pyrazolyl)-acrylic acid-N-(pyrrolidinomethyl)-amide.

21. Anti-microbial composition comprising a pharmaceutically acceptable carrier and in anti-microbially effective amount, a 3-nitropyrazole compound as claimed in claim 1.

22. Method of combatting microbial infections which method comprises administering to the afflicted subject anti-microbially effective amounts of a 3-nitropyrazole compound as claimed in claim 1.

23. Method as claimed in claim 22 wherein the compound is applied to combat microbial infections in the urinary tract.

24. Method as claimed in claim 22 wherein the compound is applied at a dosage of 250 to 1000 mg.

* * * * *